Figure 1:
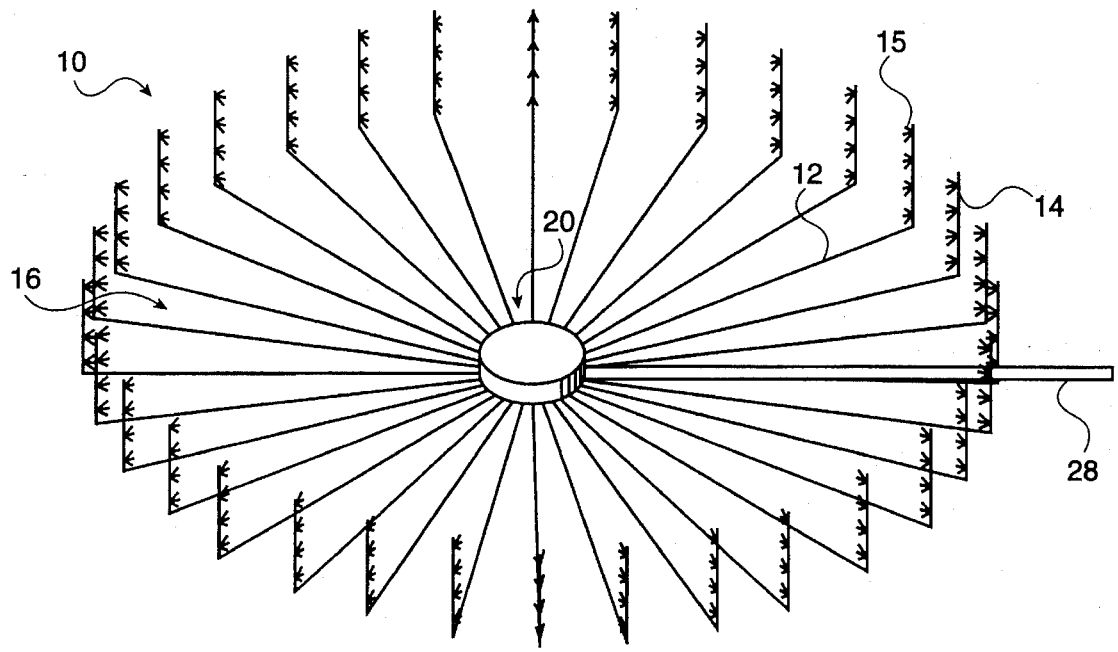
Figure 2:
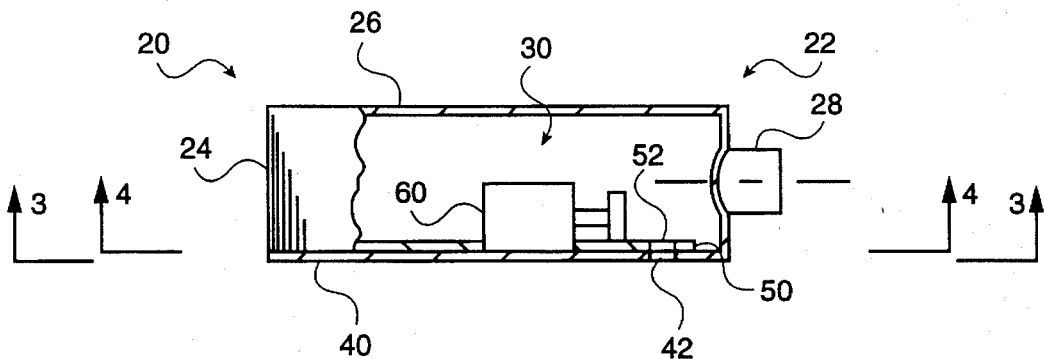
Figure 3:
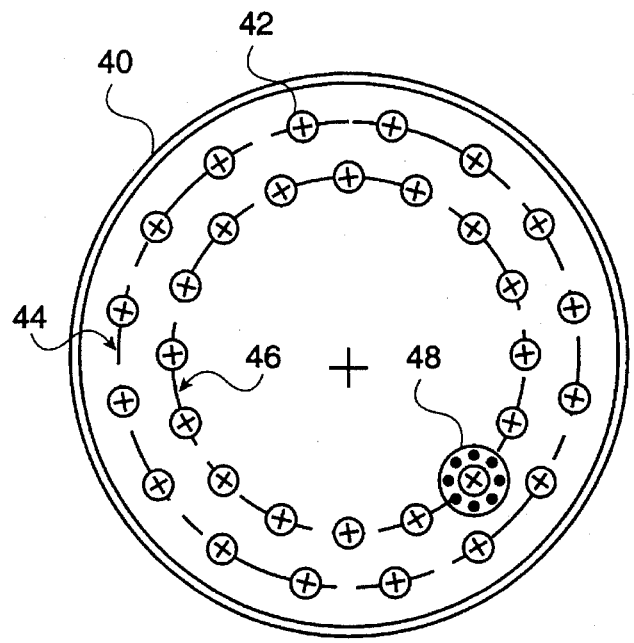
Figure 4:
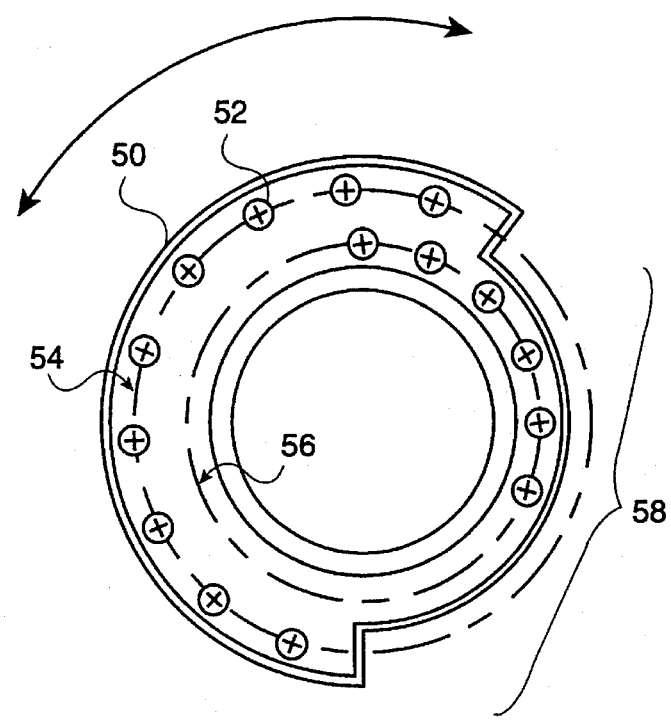

United States Patent [19]

Lewin

[11] Patent Number: 5,620,025
[45] Date of Patent: Apr. 15, 1997

[54] MULTI-PORT VALVE

[75] Inventor: Keith F. Lewin, Calverton, N.Y.

[73] Assignee: Associated Universities, Inc., Washington, D.C.

[21] Appl. No.: 347,685

[22] Filed: Dec. 1, 1994

[51] Int. Cl.⁶ ................................................. F16K 11/07
[52] U.S. Cl. ..................... 137/625.15; 137/78.5
[58] Field of Search ............................ 137/78.5, 625.11, 137/625.12, 625.13, 625.15

[56] References Cited

U.S. PATENT DOCUMENTS

| | | | |
|---|---|---|---|
| 2,529,491 | 11/1950 | Gadzuk | 137/78.5 X |
| 2,655,405 | 10/1953 | Lattner | 137/625.15 X |
| 2,746,430 | 5/1956 | Steen | 121/121 |
| 2,765,809 | 10/1956 | Lamar | 137/625.12 |
| 2,765,810 | 10/1956 | Bergquist | 137/625.12 |
| 2,878,829 | 3/1959 | Folmsbee | 137/588 |
| 2,918,938 | 12/1959 | Kimball | 137/625.11 |
| 2,964,061 | 12/1960 | Rawson et al. | 137/627 |
| 3,117,586 | 1/1964 | Cleaver | 137/78.5 X |
| 3,186,434 | 6/1965 | Hrdina | 137/625.11 |
| 3,238,971 | 3/1966 | Cerone | 137/625.11 X |
| 3,425,447 | 2/1969 | McCullough | 137/625.12 |
| 3,433,265 | 3/1969 | Bartholet | 137/625.18 |
| 3,451,428 | 6/1969 | Pruett | 137/625.46 |
| 3,494,175 | 2/1970 | Cusick et al. | 73/37 |
| 3,513,981 | 5/1970 | Mendelow | 210/411 |
| 3,580,283 | 5/1971 | DeVries | 137/625.18 |
| 3,642,022 | 2/1972 | Kirby | 137/119 |
| 3,929,112 | 12/1975 | Pagdin | 123/139 |
| 4,224,958 | 9/1980 | Kaplan et al. | 137/340 |
| 4,243,063 | 1/1981 | Parkison | 137/100 |
| 4,392,510 | 7/1983 | Heckmann et al. | 137/454.2 |
| 4,522,233 | 6/1985 | Mojadad | 137/625.47 |
| 4,801,265 | 1/1989 | Kratochwilla | 433/98 |

Primary Examiner—John Rivell
Attorney, Agent, or Firm—Margaret C. Bogosian

[57] ABSTRACT

A multi-port valve for regulating, as a function of ambient air having varying wind velocity and wind direction in an open-field control area, the distribution of a fluid, particularly carbon dioxide ($CO_2$) gas, in a fluid distribution system so that the control area remains generally at an elevated fluid concentration or level of said fluid. The multi-port valve generally includes a multi-port housing having a plurality of outlets therethrough disposed in a first pattern of outlets and at least one second pattern of outlets, and a movable plate having a plurality of apertures extending therethrough disposed in a first pattern of apertures and at least one second pattern of apertures. The first pattern of apertures being alignable with the first pattern of outlets and the at least one second pattern of apertures being alignable with the second pattern of outlets. The first pattern of apertures has a predetermined orientation with the at least one second pattern of apertures. For an open-field control area subject to ambient wind having a low velocity from any direction, the movable plate is positioned to equally distribute the supply of fluid in a fluid distribution system to the open-field control area. For an open-field control area subject to ambient wind having a high velocity from a given direction, the movable plate is positioned to generally distribute a supply of fluid in a fluid distribution system to that portion of the open-field control area located upwind.

7 Claims, 3 Drawing Sheets

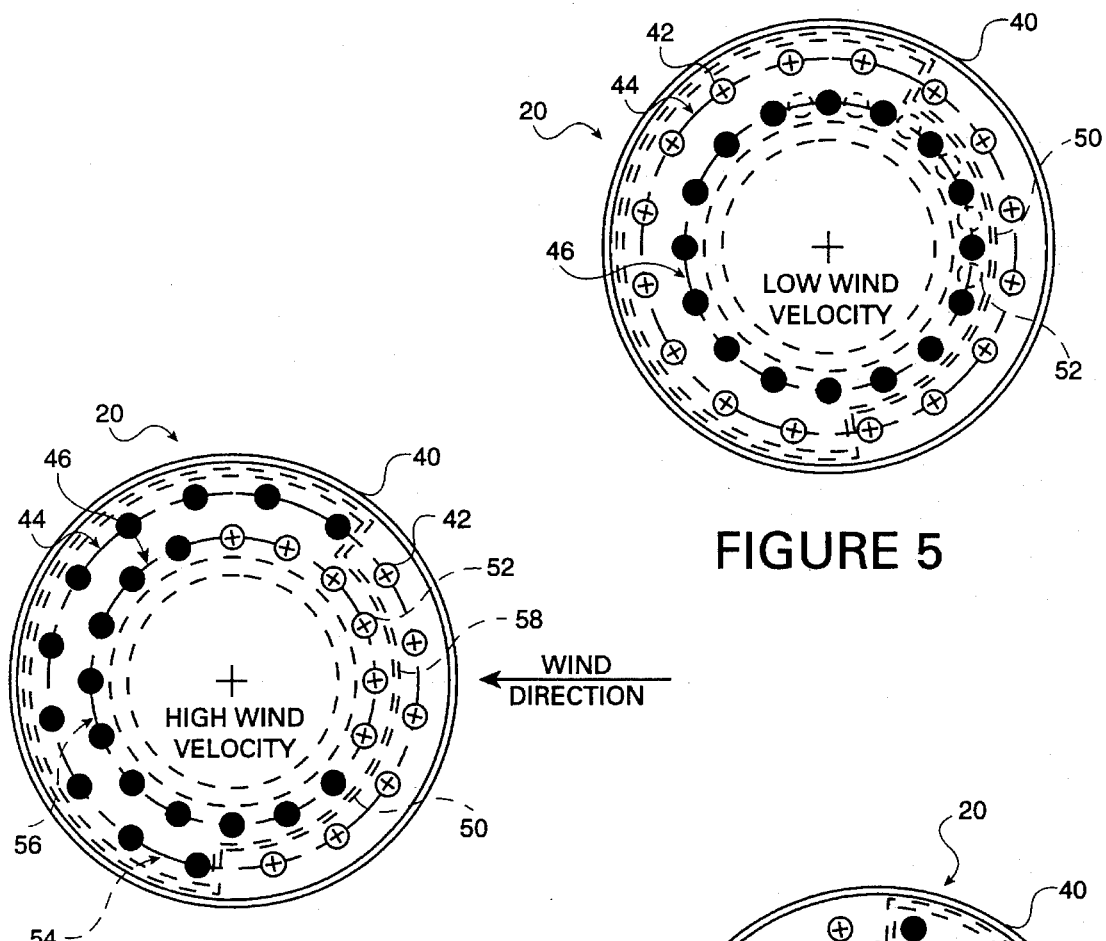

5,620,025

MULTI-PORT VALVE

This invention was made with Government support under contract number DE-AC02-76CH00016, between the U.S. Department of Energy and Associated Universities, Inc. The Government has certain rights in the invention.

BACKGROUND

The present invention relates generally to the field of multi-port valves. More particularly, this invention relates to a multi-port valve for regulating, as a function of varying wind velocity and wind direction in an open-field control area, the distribution of a fluid in a fluid distribution system.

The chemical composition of the atmosphere has changed during the last century and will continue with exasperating speed to change in the future. A major cause of this change is the burning of fossil fuel which releases carbon dioxide ($CO_2$) gas into the atmosphere. One affect of increasing levels or enrichment of $CO_2$ in the atmosphere is an expected increase in plant photosynthetic rates and plant growth.

The United States Department of Energy and the United States Department of Agriculture are conducting cooperative research into investigating the effect of increasing $CO_2$ enrichment on plants and ecosystems under a Free Air $CO_2$ Enrichment (FACE) Program. Under the program, FACE systems have been set up to controllably release $CO_2$ gas into open-field control areas. An objective of a FACE system is to maintain stable enrichment levels of $CO_2$ over an open-field control area that is hundreds of square yards in size.

A FACE system generally consists of a circular array of 32 vertically extending vent pipes in which each vent pipe includes multiple gas emitter ports. Each vent pipe in the array vertically extends from and connects to a common toroidal distribution plenum that defines a generally circular open-field control area. A blower receives and mixes pure $CO_2$ and ambient air prior to entry of the mixture into the plenum. The amount of $CO_2$ mixed with ambient air entering the plenum is determined and controlled by a computer based on measurement of the wind velocity and $CO_2$ concentration sampled at the center of the open-field control area. Emission of the $CO_2$ enriched air from each vent pipe is individually controlled by the computer as a function of measurements, varying wind velocity and wind direction, taken in the open-field control area. Studies of enriched levels of $CO_2$ in control areas containing various plants, such as cotton and pine trees, have been and continue to be conducted. In addition, pilot studies have been conducted using this same technology to enrich the atmosphere with ozone ($O_3$) and sulfur dioxide ($SO_4$).

There is a need for a multi-port valve that eliminates the need to individually control each vent pipe, to regulate, as a function of varying wind velocity and wind direction in an open-field control area, the distribution of a fluid in a fluid distribution system.

SUMMARY

It is an object of the present invention to provide a multi-port valve for regulating, as a function of varying wind velocity and wind direction in an open-field control area, the distribution of $CO_2$ or other fluid in a fluid distribution system.

It is also an object of the present invention to provide a multi-port valve that simplifies the distribution of $CO_2$ or other fluid to an open-field control area by eliminating the need to individually control each vent pipe in a fluid distribution system.

It is another object of the present invention to provide a multi-port valve that quickly and easily regulates, as a function of varying wind velocity and wind direction in an open-field control area, the distribution of a fluid in a fluid distribution system thereby reducing the usage of $CO_2$ and lowering the operating cost of the fluid distribution system in maintaining the open-field control area in a stable, enriched concentration level.

It is a further object of the present invention to provide a multi-port valve that is simple in construction and that may be manufactured easily and inexpensively.

Certain of the foregoing and related objects are readily obtained in a multi-port valve for regulating, as a function of varying wind velocity and wind direction in an open-field control area, the distribution of a fluid to a fluid distribution system. The multi-port valve generally includes a multi-port housing and a movable plate. The multi-port housing includes an inlet for receiving a fluid. The inlet is in fluid communication with a stationary plate that cooperates with the housing to form a chamber. The stationary plate includes a plurality of outlets therethrough disposed in a first pattern of outlets and at least one second pattern of outlets. The movable plate is disposed in facing relationship with the stationary plate and the movable plate includes a plurality of apertures extending therethrough disposed in a first pattern of apertures and at least one second pattern of apertures. The first pattern of apertures being alignable with the first pattern of outlets and the at least one second pattern of apertures being alignable with the second pattern of outlets. The first pattern of apertures has a predetermined orientation with the at least one second pattern of apertures.

Preferably, the plurality of outlets disposed in the first pattern of outlets is disposed along a circumference of a first circle and the at least one second pattern of outlets is disposed along a circumference of a second concentric circle, and each outlet in the first pattern of outlets along the first circle is spaced between adjacent outlets in the at least one second pattern of outlets along the second concentric circle.

Desirably, the plurality of outlets totals 32 in number and the first pattern of outlets and the second pattern of outlets each total 16 in number. Advantageously, the movable plate is rotatable and the multi-port valve includes rotatable means operatively connected to rotate the movable plate to place the plurality of apertures in a predetermined alignment with the plurality of outlets. Preferably, the rotatable means is a servo motor. The multi-port valve is ideally suitable for distributing fluid such as substantially pure carbon dioxide gas, or a mixture of ambient air having an enriched concentration level of carbon dioxide or other gaseous species, and the stationary plate includes attachment means for connecting to a plurality of tubes in a Free Air Carbon Dioxide Enrichment System.

DRAWINGS

Other objects and features of the present invention will become apparent from the following detailed description considered in connection with the accompanying drawings, which disclose several embodiments of the invention. It is to be understood that the drawings are to be used for the

3 purpose of illustration only and not as a definition of the limits of the invention. In the drawings, similar reference characters denote similar elements throughout the several views:

FIG. 1 is a perspective view of a schematically illustrated fluid distribution system that includes a multi-port valve embodying the present invention, the valve is operable to regulate, as a function of varying wind velocity and wind direction in an open-field control area, the distribution of a fluid in the fluid distribution system;

FIG. 2 is a side elevational, partial vertical cross-sectional view through a multi-port valve shown in FIG. 1;

FIG. 3 is a view taken along line 3—3 showing a stationary plate of the multi-port valve shown in FIG. 2;

FIG. 4 is a view taken along line 4—4 showing a movable plate of the multi-port valve shown in FIG. 2;

FIG. 5 is a bottom view of the multi-port valve, shown in FIGS. 1 and 2, for regulating, as a function of low wind velocity and wind in any direction in an open-field control area (FIG. 1), the distribution of a fluid in the fluid distribution system (FIG. 1), in which the stationary plate and movable plate (in phantom) shown in FIGS. 3 and 4, respectively, are positioned so that each outlet in the stationary plate is either in an opened or closed (in black) position;

FIG. 6 is similar view as shown in FIG. 5 in which the stationary plate and movable plate (in phantom) shown in FIGS. 3 and 4, respectively, are positioned so that each outlet in the stationary plate is either in an opened or closed (in black) position for high wind velocity having the direction shown by the arrow in FIG. 6; and FIG. 7 is similar view as shown in FIG. 5 in which the stationary plate and movable plate (in phantom) shown in FIGS. 3 and 4, respectively, are positioned so that each outlet in the stationary plate is either in an opened or closed (in black) position for high wind velocity having the direction shown by the arrow in FIG. 7, a direction opposite of that shown in FIG. 6.

DESCRIPTION

Turning now to the drawings and in particular to FIG. 1, which illustrates a fluid distribution system 10 that includes a multi-port valve 20 embodying the present invention. Multi-port valve 20, is operatively connected to a plurality of connecting tubes 12 extending radially outward and preferably underground to vertically extending vent pipes 14 for distributing a fluid 15, such as a carbon dioxide ($CO_2$) and air mixture, to an open-field control area 16. Specifically, in fluid distribution system 10, a plurality of vent pipes 14 are disposed radially outward from multi-port valve 20 and in equal spaced relation along the circumference of an approximately twenty-two (22) meters diameter circle to define therein open-field control area 16. Preferably, multi-port valve 20 includes thirty-two (32) vent pipes 14, each extending approximately eight (8) feet in height and each having four (4) exhaust ports for emitting fluid 15. An inlet 28, for receiving a supply of $CO_2$ and air mixture, is approximately 0.30 meter in diameter and each connecting tube 12 is approximately 0.10 meter in diameter. It will be appreciated that based on the volume of the control area 16, the type of fluid distributed, and the desired enrichment level to be maintained, that the size of the fluid distribution system 10 and multi-port valve 20, as well as the number of vent pipes 14 will vary and be equally suitable.

Referring now to FIGS. 1 and 2, multi-port valve 20 generally includes a housing 22 and a movable plate 50. Incorporation of multi-port valve 20 into fluid distribution system 10, enables quickly and easily regulating, as a function of varying wind velocity and wind direction in open-field control area 16, the distribution of fluid 15 in fluid distribution system 10 so that the control area is maintained at a substantially constant enrichment level.

Housing 22 includes a hollow cylindrical body 24 suitably attached to a top plate 26 and to a stationary plate 40 to form a chamber 30. Body 24 includes an inlet 28 for receiving a fluid to be distributed through stationary plate 40 as a function of the position of movable plate 50 with respect to stationary plate 40. Preferably, housing 20 is fabricated from metal (steel, aluminum, or brass) or suitable plastic material.

Referring to FIG. 3, stationary plate 40 has a plurality of outlets 42 extending therethrough, only one of which is numbered in FIG. 3, disposed in a first pattern of outlets 42 and a second pattern of outlets 42. Specifically, the first pattern of outlets 42 are disposed in stationary plate 40 in equal spaced relation along a circumference of an outer circle 44. The second pattern of outlets 42 are disposed in stationary plate 40 in equal spaced relation along a circumference of an inner concentric circle 46. As shown in FIG. 3, each outlet 42, in the first pattern of outlets 42 along outer circle 44, is generally spaced between each adjacent outlet 42 in the second pattern of outlets 42 disposed along inner concentric circle 46. For incorporation of multi-port valve 20 (FIG. 1) in fluid distribution system 10 (FIG. 1), each outlet 42 of stationary plate 40 includes attachment means for connecting to connecting tubes 12 (FIG. 1). A suitable fitting 48, only one shown in FIG. 3, attaches to respective lengths of connecting tube 12 (FIG. 1) that connects to a respective vent pipe 14 (FIG. 1) to discharge fluid 15 (FIG. 1) to open-field control area 16 (FIG. 1).

Referring now to FIG. 4, movable plate 50 has a plurality of apertures 52 extending therethrough, only one of which is numbered in FIG. 4, disposed in a first pattern of apertures 52 in equal spaced relation along a circumference of an outer circle 54, and a second pattern of apertures 52 disposed along a circumference of an inner circle 56. Referring to FIGS. 3 and 4, the first pattern of apertures 52 in movable plate 50 is alignable with the first pattern of outlets 42 in stationary plate 40. The second pattern of apertures 52 in movable plate 50 is alignable with the second pattern of outlets 42 in stationary plate 40. Movable plate 50 further has a partial arcuate cutout 58 disposed to register with outer circle 44 in stationary plate 40. In addition, the first pattern of apertures 52 and the second pattern of apertures 52 are disposed to have a predetermined registration with respect to each other.

Referring specifically to FIGS. 2–4, movable plate 50 is disposed in facing relationship to stationary plate 40. Desirably, as shown in FIG. 2, multi-port valve 20 includes rotatable means operatively connected to rotate movable plate 50 to place the plurality of apertures 52 (FIG. 4) in a predetermined alignment with the plurality of outlets 42 (FIG. 3). Preferably, the rotatable means includes a servo motor 60. Movable plate 50 is preferably fabricated from a suitable metal (steel, aluminum or brass) or a suitable plastic material.

Referring to FIGS. 1 and 5–7, in operation of multi-port valve 20 for regulating, as a function of varying wind velocity and wind direction in open-field control area 16, the distribution of fluid 15 in fluid distribution system 10, movable plate 50 is rotated with respect to stationary plate

40. Specifically, in FIG. 5, movable plate 50 is positioned with respect to stationary plate 40 to distribute fluid 15 (FIG. 1) to open-field control area 16 (FIG. 1) subject to wind having a low velocity from any direction. Wind having a low velocity is typically in the range less than 0.40 meters per second. In FIGS. 6 and 7, movable plate 50 is positioned with respect to stationary plate 40 to distribute fluid 15 to open-field control area 16 (FIG. 1) subject to wind having a high velocity. Wind having a high velocity is typically in the range of 0.40 meters per second or greater. As shown in each FIGS. 6 and 7, the direction of wind at high velocity is represented by the arrows, shown in the respective figures. The wind direction shown in FIG. 7 is opposite to that shown in FIG. 6.

Specifically referring to FIG. 5, movable plate 50, shown in phantom, is positioned so that certain outlets 42 in stationary plate 40 are either in an open or closed (in black) position to equally distribute fluid 15 (FIG. 1) to open-field control area 16 (FIG. 1). Specifically, each outlet 42 in stationary plate 40 along inner concentric circle 46 is closed while every outlet 42 disposed along outer circle 44 is open. Outlets 42 which are open correspond to a connecting tube 12 connected between it and, respectively, every other vent pipe 14 (FIG. 1) in fluid distribution system 10 (FIG. 1). In this configuration, shown in FIG. 5, open-field control area (FIG. 1) can be easily maintained in a constant elevated fluid concentration level (of fluid 15) while experiencing wind having a low velocity from any direction.

As shown in FIG. 6, movable plate 50, shown in phantom, is positioned so that certain outlets 42 in stationary plate 40 are either in an open or closed position to generally distribute fluid 15 (FIG. 1) to a selected portion of open-field control area 16 (FIG. 1) so that fluid 15 (FIG. 1) is directed through the respective connecting tubes 12 and vent pipes 14 to that portion of open-field control area 16 (FIG. 1) which is located upwind. Specifically, outlets 42 which are open correspond to vent pipes 14 (FIG. 1) disposed upwind while outlets 42 which are closed correspond to vent pipes 14 (FIG. 1) disposed downwind. More specifically, apertures 52, disposed along the circumference of inner circle 56 in movable plate 50, are in registration with outlets 42 along inner concentric circle 46 in stationary plate 40. Apertures 52, disposed along the circumference of outer circle 54 in movable plate 50, are not in registration with outlets 42 along outer concentric circle 44 in stationary plate 40 and only outlets 42, disposed along outer concentric circle 46 which align with cutout 58 in movable plate 50, are open.

For a change in direction of the wind having a high velocity, movable plate 50 can be easily rotated to properly adjust the distribution of fluid 15 (FIG. 1) to another selected area of open-field control area 16 (FIG. 1). As shown in FIG. 7, the direction of wind having a high velocity is oppositely directed compared to the wind direction shown in FIG. 6. In FIG. 7, movable plate 50 is rotated 180° compared to FIG. 6. Desirably, servo motor 60 (FIG. 2) is operatively connected to a computer (not shown) that detects and monitors the wind velocity and wind direction, and accordingly, adjusts the position of movable plate 50 for the proper distribution of fluid 15 (FIG. 1) to selected areas at the upwind side(s) of open-field control area 16 (FIG. 1).

Preferably, as shown in FIGS. 6 and 7, for conditions in which the wind has a high velocity, twelve (12) outlets 42 which are connected by connecting tubes 12 to vent pipes 14 directly upwind are held in an open position. Eight (8) outlets 42 of the twelve (12) outlets 42 are adjacent to each other and directly upwind (i.e., outlets 42 connected to upwind vent pipes 14 by connecting tubes 12). It will be appreciated that other distribution configurations, such as all outlets which correspond to upwind vent pipes 14, for distributing a fluid to an open-field control area subjected to wind having a high velocity can be equally well employed.

It will be further appreciated that multi-port valve 20 can be reduced in size in the case where the enrichment fluid, such as $CO_2$, $O_3$, $SO_4$, or other fluid to be regulated by multi-port valve 20 is substantially pure in composition (i.e., not initially mixed with ambient air). Accordingly, connecting tubes 14 can also be reduced in size.

Thus, while only several embodiments of the present invention have been shown and described, it is obvious that many changes and modification may be made thereunto without departing from the spirit and scope of the invention.

I claim:

1. A valve for regulating, as a function of ambient air having varying wind velocity and wind direction in an open-field control area, the distribution in a variety of patterns of a fluid in a fluid distribution system, the valve comprising:

a multi-port housing having an inlet for receiving a fluid, said inlet being in fluid communication with a stationary plate that cooperates with said housing to form a chamber, said stationary plate having a plurality of outlets therethrough disposed in a first pattern of outlets and at least one second pattern of outlets, said stationary plate further including attachment means for connecting each of the outlets in said first and second patterns, respectively, to a separate one of a plurality of tubes each having a respective distal end disposed adjacent the circumference of said open-field control area at a point spaced from other tubes in the plurality of tubes;

a movable plate disposed in facing relationship with said stationary plate, said movable plate having a plurality of apertures extending therethrough disposed in a first pattern of apertures and at least one second pattern of apertures, said first pattern of apertures being selectively alignable relative to said first pattern of outlets and said at least one second pattern of apertures being selectively alignable relative to said second pattern of outlets, said first pattern of apertures having a predetermined orientation with said at least one second pattern of apertures;

said valve further including rotatable means operatively connected to selectively rotate said movable plate to a predetermined number of positions relative to said plurality of outlets, whereby in a first of such positions all of the outlets in the first pattern of outlets are open and all of the outlets in the second pattern are closed thereby to equally distribute fluid to the open-field control area.

2. A valve as defined in claim 1 wherein said movable plate has a partial arcuate cutout disposed to register with and thereby open selected outlets in the first pattern of outlets in the stationary plate responsive to operation of the rotatable means moving the movable plate to effect such a registration, and wherein rotation of said plate to a second of such positions opens only certain other outlets in the first and second patterns and closes the remaining outlets except for those in registration with said arcuate cutout, thereby to distribute fluid to only a portion of the open-field control area that is located on an upwind first side of said area.

3. A valve as defined in claim 2 wherein in a third of such positions only certain further outlets in the first and second patterns are open and the remaining outlets are closed except for those in registration with said arcuate cutout, thereby to distribute fluid to only a portion of the open-field control area that is located on a second side thereof.

4. A valve as defined in claim 3 wherein the number of outlets open in the first and second patterns is the same in both said second and third positions.

5. A valve as defined in claim 3 wherein said arcuate cutout can only be disposed in registration with less that one-half of the outlets in said stationary plate in any of the positions to which the movable plate can be rotated.

6. A valve as defined in claim 2 wherein said predetermined number of positions is at least equal to the number of outlets in the pattern of outlets having the smallest number of outlets.

7. A valve as defined in claim 6 wherein said predetermined number of positions is at least equal to the number of outlets in the pattern of outlets having the largest number of outlets, whereby complex varieties of area patterns within the open-field control area is selectively provided with fluid corresponding to different positions of said plate.

* * * * *